United States Patent
Cortez, Jr. et al.

(10) Patent No.: US 8,171,935 B2
(45) Date of Patent: May 8, 2012

(54) NASAL CANNULA WITH REDUCED HEAT LOSS TO REDUCE RAINOUT

(75) Inventors: Felino V. Cortez, Jr., Bowie, MD (US); William F. Niland, Arnold, MD (US); Carl Buyer, Denton, MD (US); George McGarrity, Denton, MD (US)

(73) Assignee: Vapotherm, Inc., Stevensville, MD (US)

( * ) Notice: Subject to any disclaimer, the term of this patent is extended or adjusted under 35 U.S.C. 154(b) by 1061 days.

(21) Appl. No.: 11/940,867

(22) Filed: Nov. 15, 2007

(65) Prior Publication Data

US 2008/0121230 A1 May 29, 2008

Related U.S. Application Data

(60) Provisional application No. 60/859,222, filed on Nov. 15, 2006.

(51) Int. Cl.
*A62B 7/00* (2006.01)
(52) U.S. Cl. ......... 128/207.18; 128/203.26; 128/204.17; 128/205.25; 128/206.21; 128/207.13
(58) Field of Classification Search .............. 128/200.24, 128/203.12, 203.26, 203.27, 204.17, 204.18, 128/205.25, 206.21, 207.13, 207.18
See application file for complete search history.

(56) References Cited

U.S. PATENT DOCUMENTS

| | | | |
|---|---|---|---|
| 2,735,432 A * | 2/1956 | Hudson | 128/207.18 |
| 2,868,199 A | 1/1959 | Hudson | |
| 3,513,844 A * | 5/1970 | Smith | 128/207.18 |
| 3,726,275 A | 4/1973 | Jackson et al. | |
| 3,802,431 A | 4/1974 | Farr | |
| 4,106,505 A | 8/1978 | Salter et al. | |
| 4,273,124 A | 6/1981 | Zimmerman | |
| 4,278,082 A | 7/1981 | Blackmer | |
| 4,422,456 A | 12/1983 | Tiep | |
| 4,535,767 A | 8/1985 | Tiep et al. | |
| 4,648,398 A | 3/1987 | Agdanowski et al. | |

(Continued)

FOREIGN PATENT DOCUMENTS

WO    WO-00/64521    11/2000

(Continued)

OTHER PUBLICATIONS

Partial International Search Report for PCT International Application No. PCT/US2007/023973.

(Continued)

*Primary Examiner* — Justine Yu
*Assistant Examiner* — LaToya M Louis
(74) *Attorney, Agent, or Firm* — RatnerPrestia

(57) ABSTRACT

A system for delivering a humidified gas to a patient is disclosed. The system includes a supply tube having a first supply tube end and a second supply tube end. The supply tube has a first inner diameter. The system also includes an apparatus for delivering heated and humidified gas to the first end of the supply tube and a single lumen having a first lumen end and a second lumen end. The single lumen has a second inner diameter, smaller than the first diameter. The first lumen end is in fluid flow communication with the second supply tube end. The system also includes a nasal cannula in fluid flow communication with the second lumen end. A method of delivering heated and humidified gas to a patient is also disclosed.

9 Claims, 18 Drawing Sheets

U.S. PATENT DOCUMENTS

| | | | |
|---|---|---|---|
| 4,753,233 | A | 6/1988 | Grimes |
| 4,808,160 | A | 2/1989 | Timmons et al. |
| 4,995,384 | A * | 2/1991 | Keeling .................. 128/207.18 |
| 5,025,805 | A | 6/1991 | Nutter |
| 5,046,491 | A * | 9/1991 | Derrick ................... 128/200.24 |
| 5,509,409 | A | 4/1996 | Weatherholt |
| 5,526,806 | A | 6/1996 | Sansoni |
| 6,655,385 | B1 | 12/2003 | Curti et al. |
| 6,679,265 | B2 | 1/2004 | Strickland et al. |
| 6,763,832 | B1 | 7/2004 | Kirsch et al. |
| 6,776,163 | B2 | 8/2004 | Dougill et al. |
| 6,799,575 | B1 | 10/2004 | Carter |
| 7,146,979 | B2 | 12/2006 | Seakins et al. |
| 2002/0157673 | A1 * | 10/2002 | Kessler et al. .......... 128/207.18 |
| 2004/0035430 | A1 | 2/2004 | Wright |
| 2005/0161049 | A1 | 7/2005 | Wright |
| 2006/0005842 | A1 * | 1/2006 | Rashad et al. .......... 128/207.18 |
| 2008/0051674 | A1 * | 2/2008 | Davenport et al. .......... 600/561 |

FOREIGN PATENT DOCUMENTS

| | | |
|---|---|---|
| WO | WO-2005/011556 | 2/2005 |
| WO | WO-2006/072231 | 7/2006 |
| WO | WO-2007/111935 | 10/2007 |

OTHER PUBLICATIONS

International Search Report for PCT International Application No. PCT/US2007/023973 mailed Aug. 12, 2008.

Written Opinion of the International Searching Authority for PCT International Application No. PCT/US2007/023973 mailed Aug. 12, 2008.

* cited by examiner

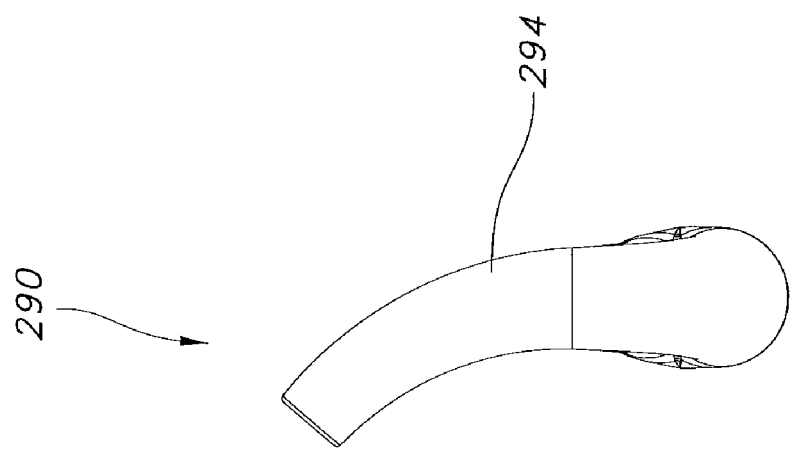
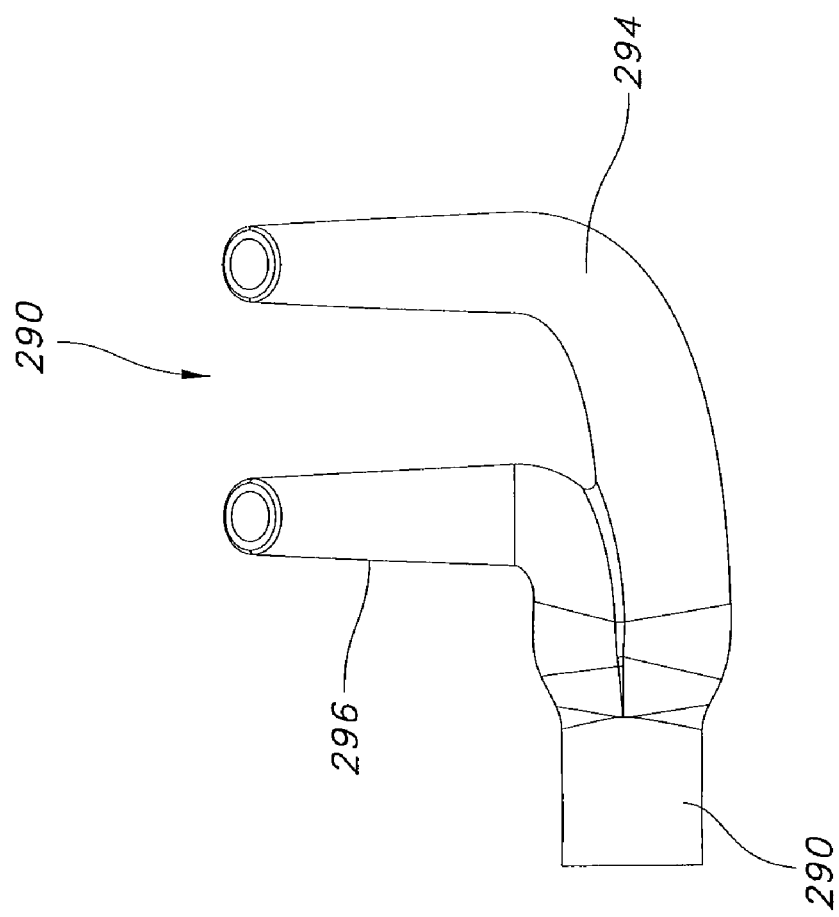

NASAL CANNULA WITH REDUCED HEAT LOSS TO REDUCE RAINOUT

CROSS-REFERENCE TO RELATED APPLICATION

The present application claims priority from U.S. Provisional Patent Application Ser. No. 60/859,222, filed on Nov. 15, 2006, which is incorporated by reference herein in its entirety.

BACKGROUND OF THE INVENTION

Delivery of oxygen and oxygen-enriched air to the respiratory tract of a patient can result in discomfort to the patient, especially when the air is delivered over an extended period of time. Delivery of air having relatively low absolute humidity can also result in respiratory irritation.

When heating and humidifying a breathing gas for breathing through a nasal cannula, any cooling in the nasal cannula may lead to excessive condensation within the nasal cannula. When excessive condensation is present within the nasal cannula, drops of liquid water may subsequently be delivered to the patient's nose.

SUMMARY OF THE INVENTION

Briefly, the present invention provides a system for delivering a heated and humidified gas to a patient. The system comprises a supply tube having a first supply tube end and a second supply tube end. The supply tube has a first inner diameter. A source of humidified gas is coupled to the first supply tube end for delivering gas through the first inner diameter of the supply tube. A connector has a first connector end in fluid flow communication with the second supply tube end and a second connector end is in fluid flow communication with the first connector end and has a second inner diameter, smaller than the first inner diameter. A nasal cannula is in fluid flow communication with the second connector end.

Additionally, the present invention provides a method of delivering heated and humidified gas to a patient while reducing rainout comprising the steps of: generating a heated and humidified gas; and flowing the humidified gas toward a nasal passage of a patient through a single conduit, wherein a downstream inner diameter of the single conduit is smaller than an upstream inner diameter of the single conduit.

Further, the present invention provides a nasal cannula. The nasal cannula comprises a nasal element having a first element end, a second element end, and a generally tubular body extending between the first element end and the second element end. A lumen has a first lumen end in fluid flow communication with the first element end, and a second lumen end. A connector has a first connector end in fluid flow communication with the second lumen end. A closed medium has a first closed medium end fixedly coupled to the second element end and a second closed medium end fixedly coupled to the first connector end.

Also, the present invention provides a method of reducing heat loss and rainout in a nasal cannula comprising the steps of generating heated and humidified gas and flowing the heated and humidified gas toward a nasal passage of a patient through a single conduit having an upstream inner diameter of the single conduit and a downstream inner diameter smaller than the upstream inner diameter.

Further, the present invention also provides a nasal cannula. The nasal cannula comprises a nasal element having a first element end, a second element end, and a generally tubular body extending between the first element end and the second element end. A first lumen extends from the first element end and a second lumen extends from the second element end. A connector is coupled to the first lumen and the second lumen. Fluid flow is provided between the connector and the nasal element through only the first lumen.

The present invention further provides a method of delivering heated and humidified gas to a patient comprising the steps of generating heated and humidified gas; flowing the heated and humidified gas toward a nasal passage of a patient through a conduit; and disposing the conduit against the skin of the patient, thereby reducing a temperature gradient of the heated and humidified gas along the conduit

BRIEF DESCRIPTION OF THE DRAWINGS

The foregoing summary, as well as the following detailed description of preferred embodiments of the invention, will be better understood when read in conjunction with the appended drawings, which are incorporated herein and constitute part of this specification. For the purposes of illustrating the invention, there are shown in the drawings exemplary embodiments of the invention. It should be understood, however, that the invention is not limited to the precise arrangements and instrumentalities shown. In the drawings, the same reference numerals are employed for designating the same elements throughout the several figures. In the drawings:

FIG. 8A is a front elevational view of a nasal insertion member shown in the nasal cannula of FIGS. 7 and 8;

FIG. 8B is a side elevational view of the nasal insertion member shown in FIG. 8A;

DETAILED DESCRIPTION OF THE INVENTION

Certain terminology is used herein for convenience only and is not to be taken as a limitation on the present invention. The terminology includes the words specifically mentioned, derivatives thereof and words of similar import. As used herein, the term "proximal" is defined to mean a direction closer to the humidification cartridge described herein and "distal" is defined to mean a direction farther from the humidification cartridge described herein. The following describes exemplary embodiments of the invention. However, it should be understood based on this disclosure, that the invention is not limited by the exemplary embodiments of the invention.

Figure 1:
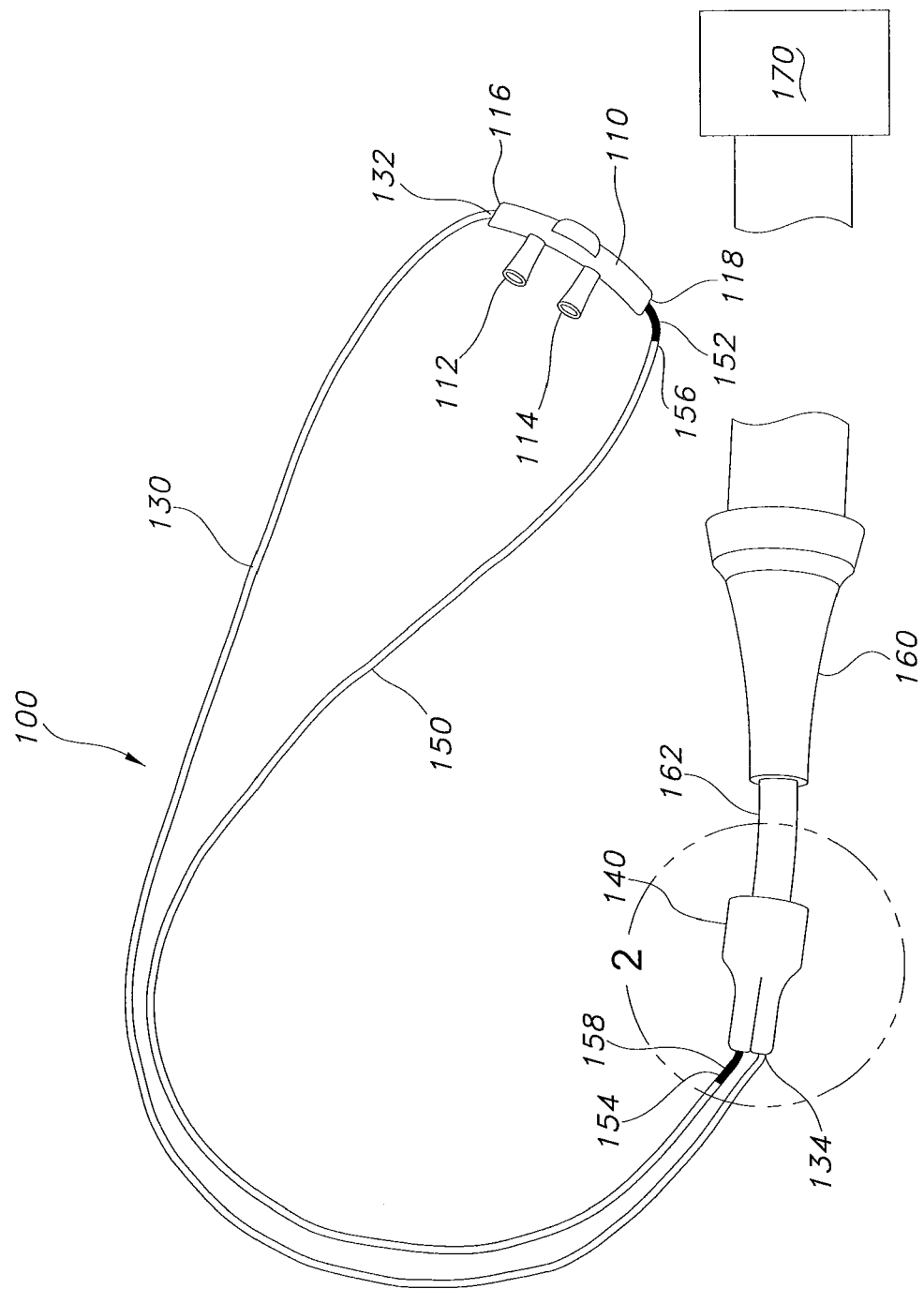
FIG. 1 is a perspective view of a first embodiment of a nasal cannula according to the present invention.
Figure 2:
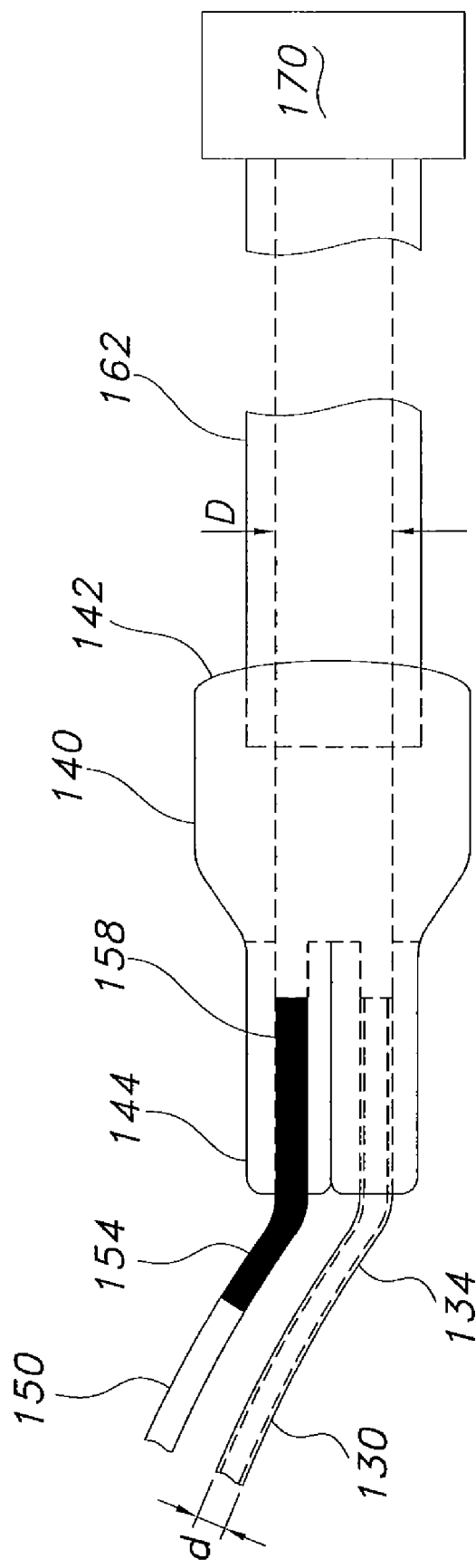
FIG. 2 is an enlarged view of a connector of the nasal cannula shown in FIG. 1.
Figure 3:
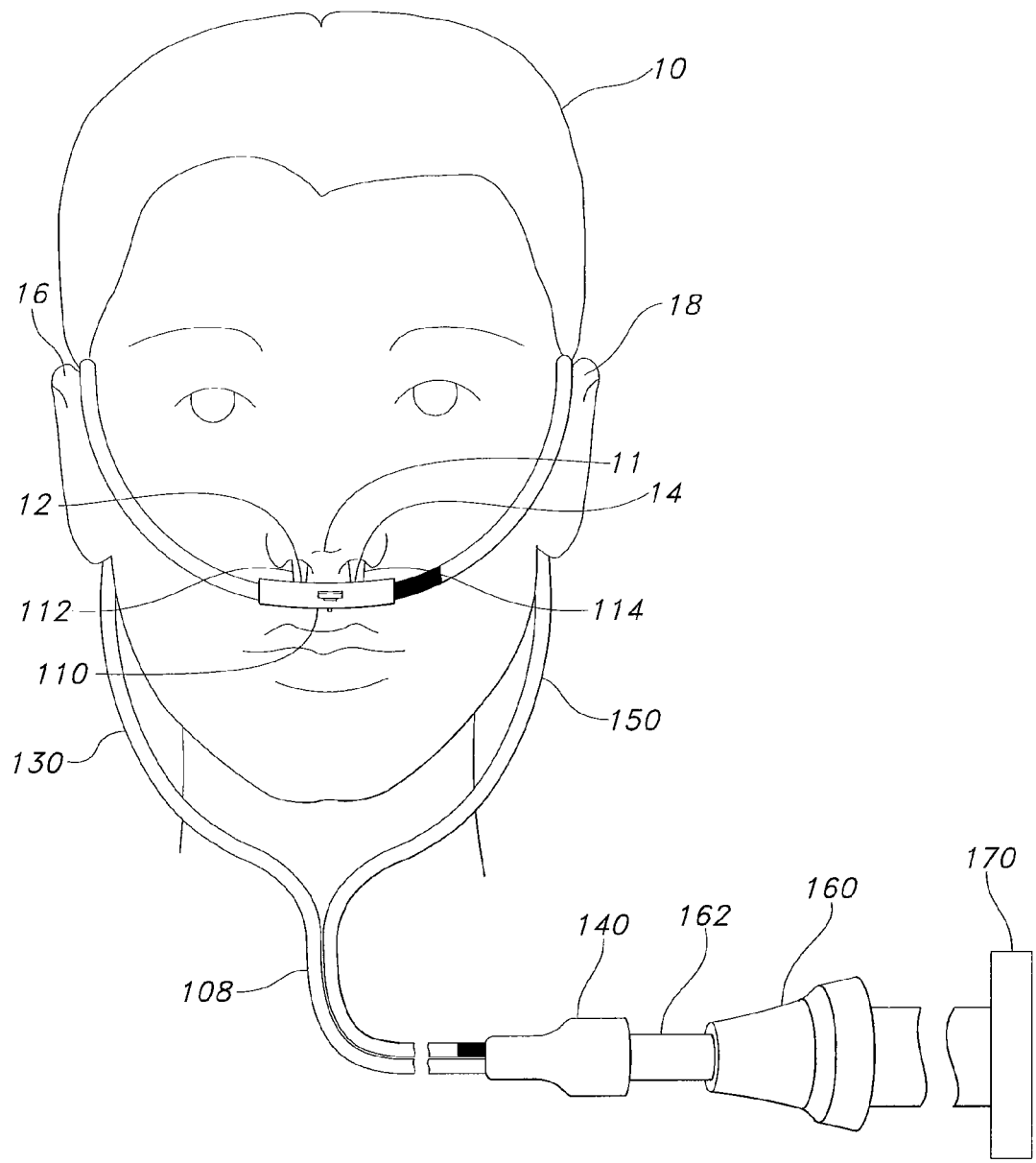
FIG. 3 is a front elevation view of the nasal cannula of FIG. 1 in use on a patient.

Referring to FIGS. 1-3 generally, a device in the form of a nasal cannula 100 is part of a conduit that is provided for delivering humidified breathing gas from a source of heated and humidified breathing gas to a patient. Nasal cannula 100 includes a nasal insertion member 110 that is used to deliver breathing gas to the patient 10. Nasal insertion member 110 includes two hollow open prongs 112, 114, with first prong 112 adapted for insertion into a first nare 12 and the second prong 114 adapted for insertion into a second nare 14. The nasal insertion member 110 also includes a first end 116 and a second end 118 that are in fluid flow communication with each other and also with the first and second prongs 112, 114.

In use, breathing gas is administered to a patient by fitting each nare 12, 14 of the nose 11 of the patient 10 with a prong 112, 114 of nasal cannula 100. Depending upon the respiratory therapy being applied, the breathing gas is delivered through prongs 112, 114 of nasal cannula 100 at a rate of between about 1 and about 40 liters per minute.

Additionally, the breathing gas is delivered in a humidified condition of up to 100% humidity and at an elevated temperature of between about 33.0° C. to about 43.0° C. In an exemplary embodiment, the breathing gas may be heated and humidified through a humidifier as disclosed in U.S. patent application Ser. No. 10/149,356, which is owned by the assignee of the present invention and is incorporated herein by reference as though fully set forth. The humidification is accomplished by transferring water vapor across a membrane to the breathing gas being supplied to the patient 10.

A first lumen 130 is fixedly coupled to first end 116 at a first distal lumen end 132. First lumen 130 is a hollow elongated tube and fluidly communicates with the nasal insertion member 110. The first lumen 130 also includes a first proximal lumen end 134 that is fixedly coupled to a connector 140. Connector 140 connects cannula 100 to a humidification cartridge 170 via a delivery tube. An elongated flexible member 150 is fixedly coupled to second end 118 of the nasal insertion member 110 at a distal member end 152. Member 150 also includes a proximal member end 154 that is fixedly coupled to the connector 140. Member 150 does not provide for fluid flow communication between connector 140 and nasal insertion member 110. Member 150 may be a second lumen that has a first blocking portion 156 inserted in distal member end 152 and/or a second blocking portion 158 that is inserted in proximal member end 154 to preclude fluid flow through member 150.

Alternatively, member 150 may be a solid, preferably flexible, member that does not include a lumen. For example, member 150 may be a solid piece of silicone. Still alternatively, member 150 may be a material such as a suture, so long as member 150 is flexible enough to bend over the patient's ear during use. It is important that member 150 not fluidly communicate any fluid therethrough so that all of the heated and humidified breathing gas being transmitted to nasal insertion member 110 does so only through first lumen 130.

Connector 140 is shown in an enlarged view in FIG. 2. Connector 140 includes a proximal connector end 142 that is coupled to humidification cartridge 170, such as through a delivery tube 162. Proximal connector end 142 has a first inner diameter "D." Delivery tube 162 is coupled to an adapter 160, shown in FIG. 1, which connects delivery tube 162 and humidification cartridge 170, such that delivery tube 162 and humidification cartridge 170 are in fluid flow communication with each other.

Referring back to FIG. 2, connector 140 also includes a distal connector end 144 that is fixedly coupled to both first proximal lumen end 134 and proximal member end 154. As described above, proximal member end 154 may be closed to fluid flow by a second blocking portion 158. Therefore, all fluid flow is directed from distal connector end 144 into first proximal lumen end 134. First proximal lumen end 134 has a diameter "d" that is smaller than diameter "D" of proximal connector end 142.

In an exemplary embodiment, the diameter "D" is approximately 4 mm, while diameter "d" is approximately 2 mm. It has been discovered that the inventive configuration also reduces noise generated by breathing gas as the breathing gas exits first and second nasal prongs 112, 114.

In use, patient 10 inserts first and second nasal prongs 112, 114 under the nose 11 and into a respective nare 12, 14 as shown in FIG. 3. Patient 10 then wraps first lumen 130 over an ear 16 (the right ear as shown in FIG. 3) and wraps member 150 over the remaining (left) ear 18.

Heated and humidified breathing gas is provided from humidification cartridge 170, through adapter 160, through delivery tube 162, and to connector 140. At connector 140, the diameter of the fluid conduit through which the breathing gas is being supplied steps down from diameter "D" to diameter "d".

The breathing gas then travels through first lumen 130 only, since support member 150 is closed off and is unable to allow fluid flow therethrough. The breathing gas travels through first lumen 130 to nasal insertion member 110 for inhalation through nares 12, 14 and into patient's nose 11.

Figure 4:
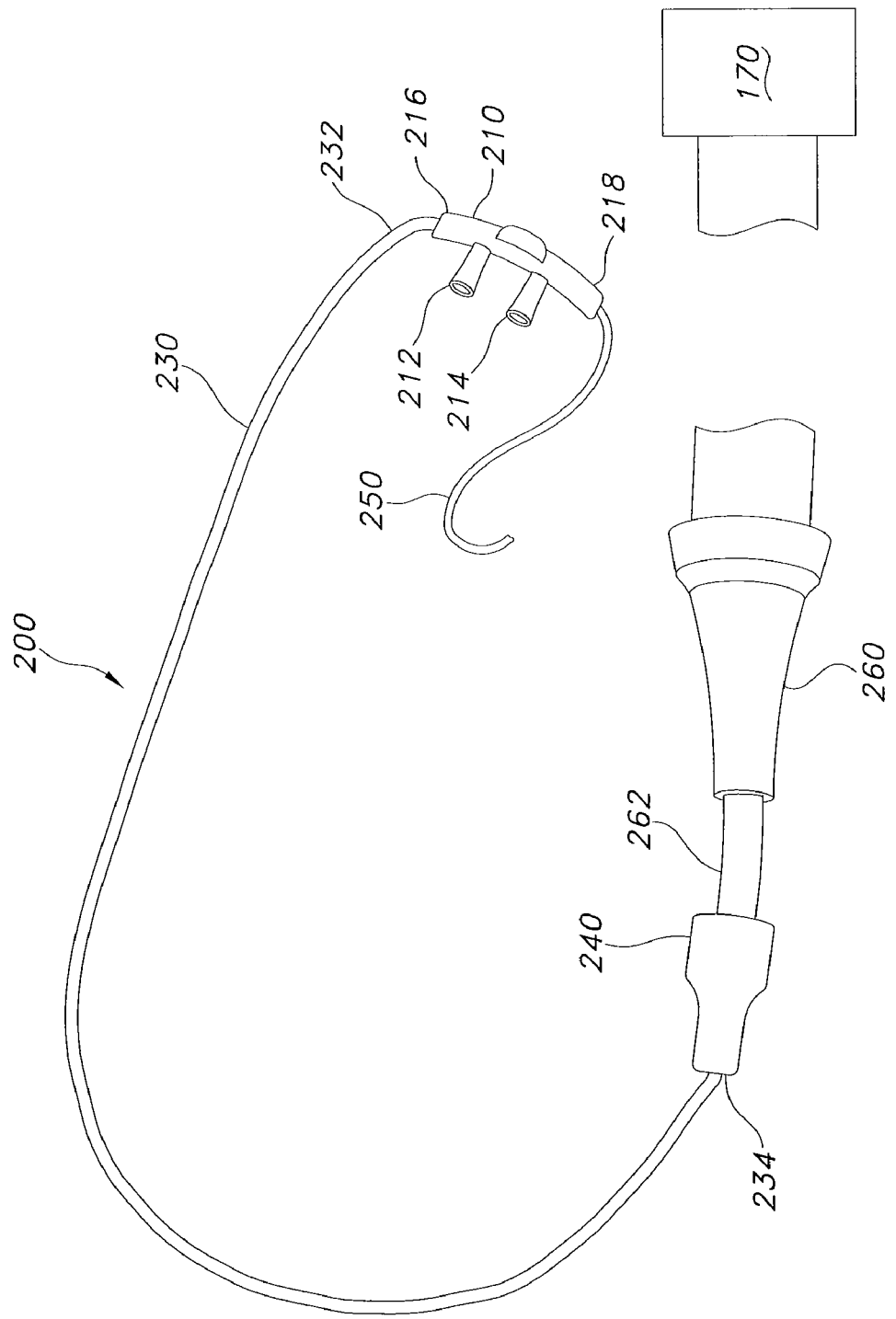
FIG. 4 is a perspective view of a second embodiment of a nasal cannula according to the present invention.
Figure 5:
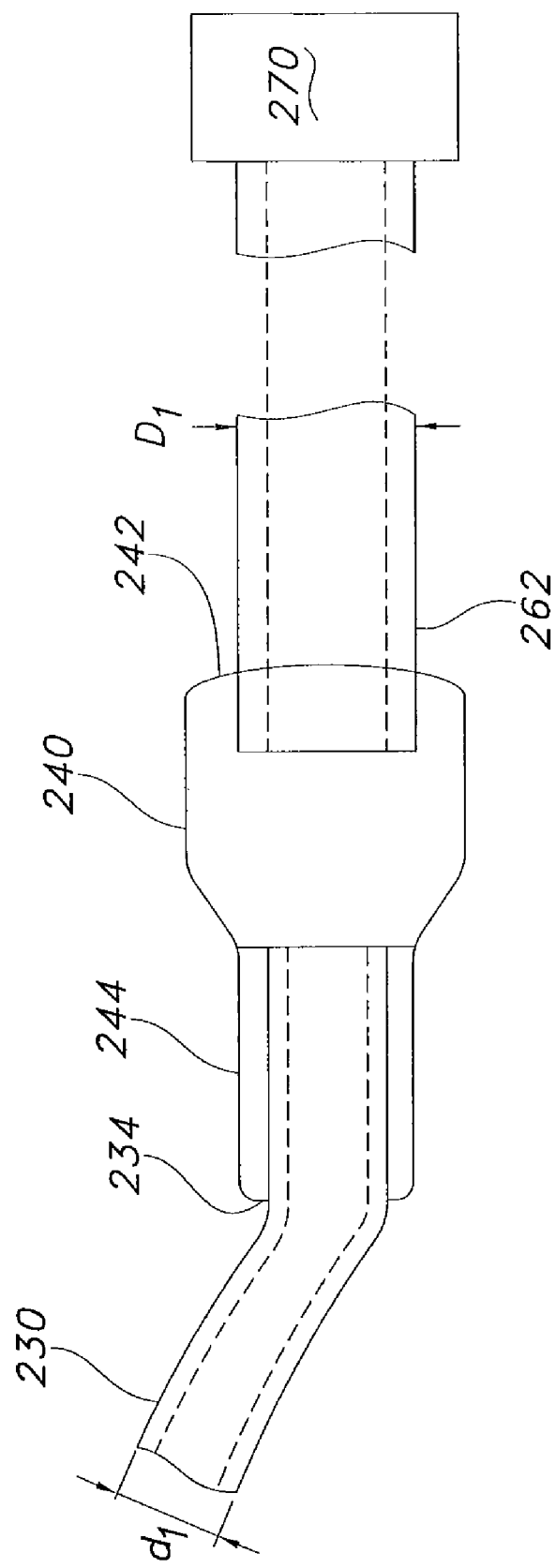
FIG. 5 is an enlarged view of a connector of the nasal cannula shown in FIG. 4.
Figure 6:
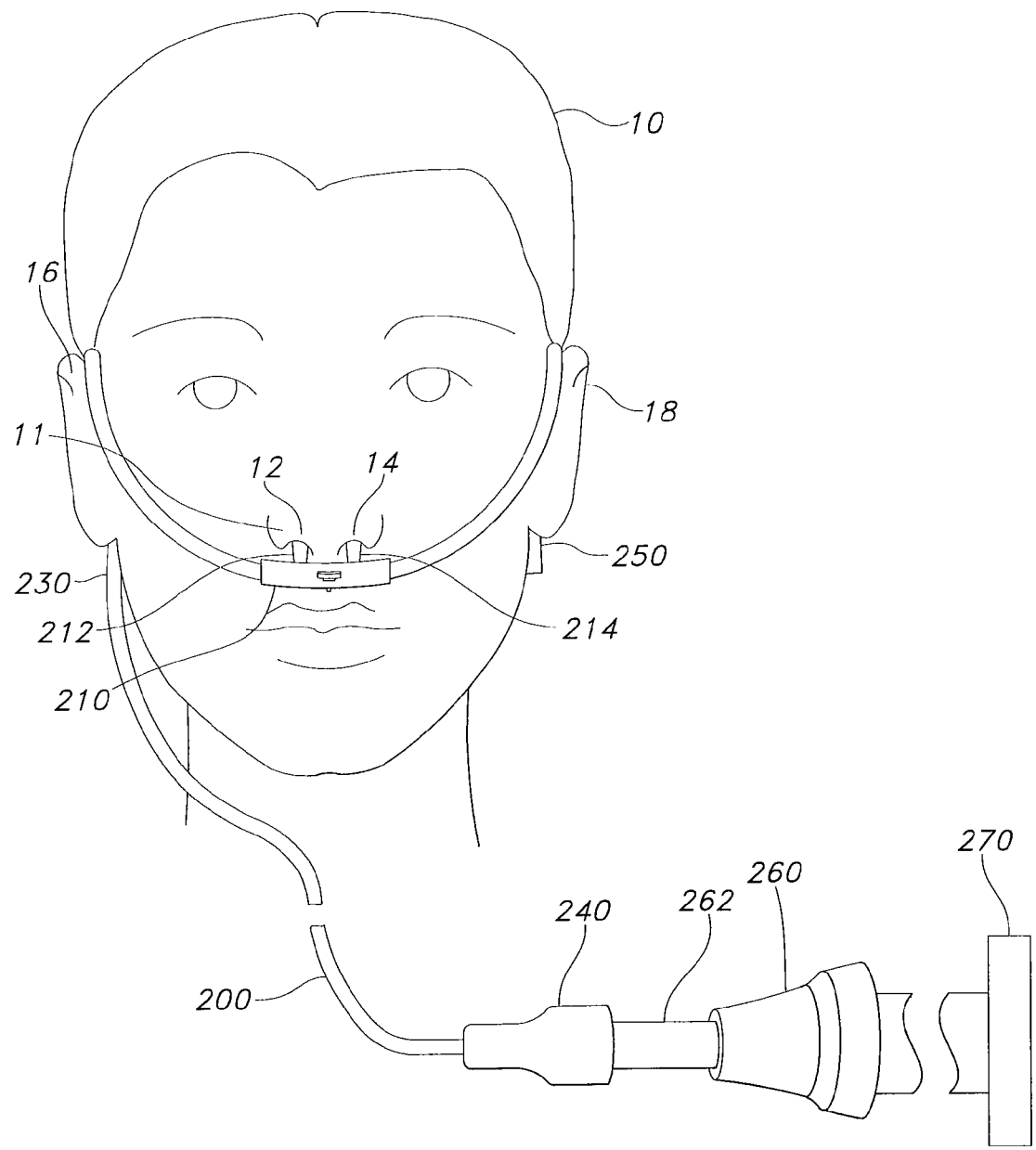
FIG. 6 is a front elevation view of the nasal cannula of FIG. 4 in use on a patient.

An alternate exemplary embodiment of a nasal cannula 200 according to the present invention is shown in FIGS. 4-6. The cannula 200 includes a nasal insertion member 210 having first and second nasal prongs 212, 214. The nasal insertion member 210 also includes a first end 216 and a second end 218 that are in fluid flow communication with each other and also with the first and second prongs 212, 214.

A first lumen 230 is fixedly coupled to first end 216 at a first distal lumen end 232. First lumen 230 is a hollow elongated tube and fluidly communicates with nasal insertion member 210. First lumen 230 also includes a first proximal lumen end 234 that is fixedly coupled to a connector 240.

Connector 240 is shown in an enlarged view in FIG. 5. Connector 240 includes a proximal connector end 242 that is coupled to a humidification cartridge 270, such as through a delivery tube 262. Proximal connector end 242 has a first inner diameter "D1." Delivery tube 262 is coupled to an adapter 260 (shown in FIG. 4), which connects delivery tube 262 and humidification cartridge 270, such that delivery tube 262 and humidification cartridge 270 are in fluid flow communication with each other.

Connector 240 also includes a distal connector end 244 that is fixedly coupled to first proximal lumen end 234. First proximal lumen end 234 has a diameter "d1" that is smaller than the diameter "D1" of proximal connector end 242. In an exemplary embodiment, the diameter "D1" is approximately 4 mm, while the diameter "d1" is approximately 3 mm. Referring back to FIG. 4, an extension 250 is fixedly coupled to second end 218. Since first lumen 230 is the only source of heated and humidified breathing gas between connector 240 and nasal insertion member 210, earpiece 250 need not necessarily extend from nasal insertion member 210 to connector 240.

As shown in FIG. 6, earpiece 250 only needs to extend sufficiently far from nasal insertion member 210 to extend over patient's ear 18 and support nasal insertion member 210 under patient's nose 11. In an exemplary embodiment, earpiece 250 is constructed from a bendable and shapeable material, such as metal wire, in order to allow earpiece 250 to be shaped to contour comfortably around patient's ear 18. Optionally, earpiece 250 may be coated, such as with a silicone coating, in order to minimize discomfort to patient 10.

In use, patient 10 inserts first and second nasal prongs 212, 214 under nose 11 and into a respective nare 12, 14 as shown in FIG. 6. Patient 10 then wraps first lumen 230 over an ear 16 (the right ear as shown in FIG. 6) and wraps earpiece 250 over the remaining (left) ear 18.

Humidified breathing gas is provided from humidification cartridge 270, through adapter 260, through delivery tube 262, and to connector 240. At connector 240, the diameter of the fluid conduit through which the breathing gas is being supplied reduces from diameter "D1" to diameter "d1".

The breathing gas travels through first lumen 230 to nasal insertion member 210 for inhalation from first and second nasal prongs 212, 214, through nares 12, 14 and into patient's nose 11.

Figure 7:
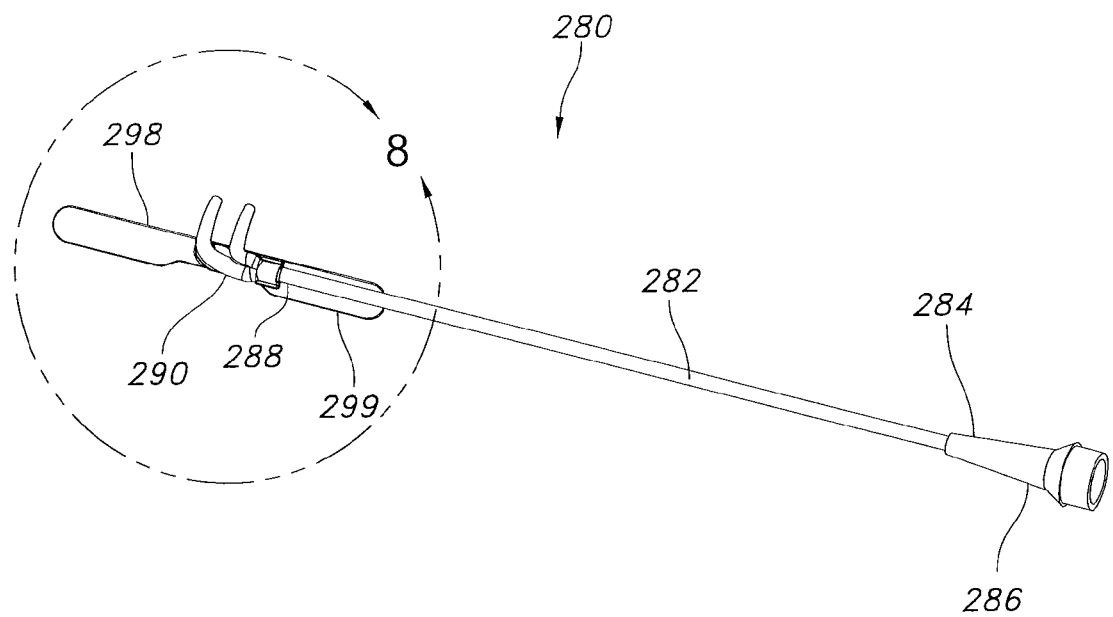
FIG. 7 is a perspective view of a nasal cannula according to another embodiment of the present invention.

Another embodiment of a nasal cannula 280 is shown in FIG. 7. Nasal cannula 280 includes a single lumen 282. Lumen 282 has a proximal end 284 that is coupled to a hub 286 and a distal end 288 that is coupled to a dual prong nasal element 290. Hub 286 may be releasably coupled to a delivery tube (not shown).

Figure 8:
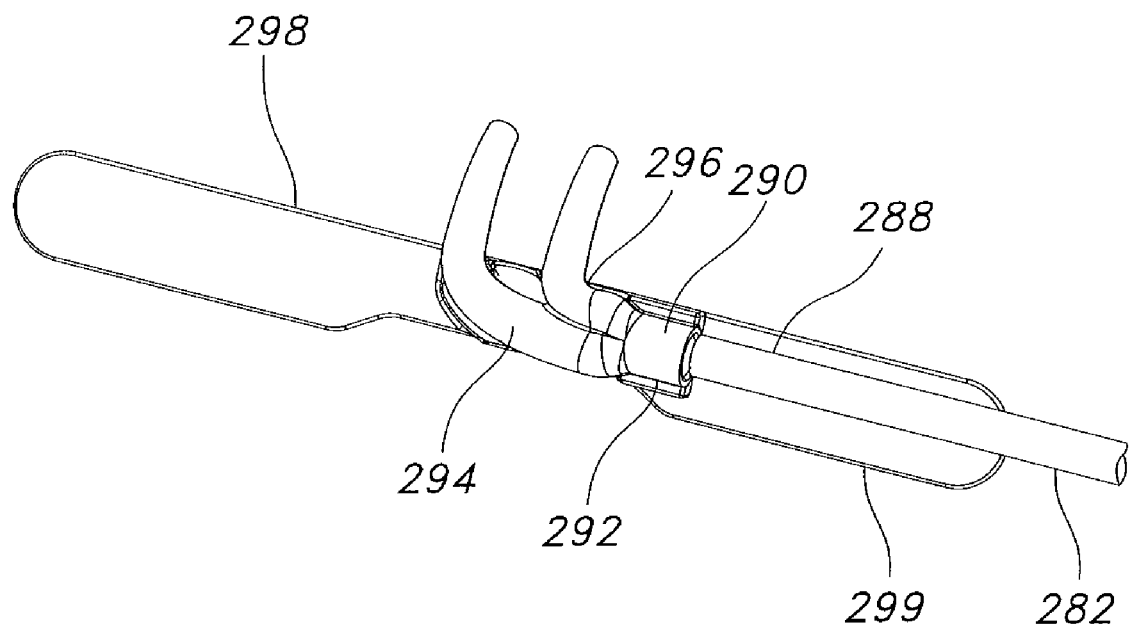
FIG. 8 is an enlarged portion of the cannula of FIG. 7, taken along line 8 of FIG. 7.

As shown in the enlargement of nasal element 290 in FIG. 8, nasal element 290 includes a cylindrical coupler 292 that is coupled to distal end 288. A pair of nasal lumens 294, 296 extends distally from coupler 292 and are in fluid communication with lumen 282. Nasal lumens 294, 296 each curve about ninety degrees and provide a smooth transition of breathing gas flow within nasal lumens 294, 296 from a direction along lumen 282 is it is shown in FIGS. 7 and 8 to a direction generally orthogonal to lumen 282.

Nasal element 290 is shown in FIGS. 8A and 8B. As FIGS. 8A and 8B show, nasal lumens 294, 296 taper from a larger diameter to a smaller diameter. Nasal lumens 294, 296 each also include a curved body at discharge ends thereof. Nasal lumens 294, 296 change direction via smooth curves between coupler 292 and the respective discharge ends to the user.

Adhesive strips 298, 299 extend from nasal element 290. A first adhesive strip 298 extends away from lumen 282 and a second adhesive strip 299 extends along lumen 282. Adhesive strips 298, 299 are used to releasably secure cannula 280 to a user during use.

Figure 9:
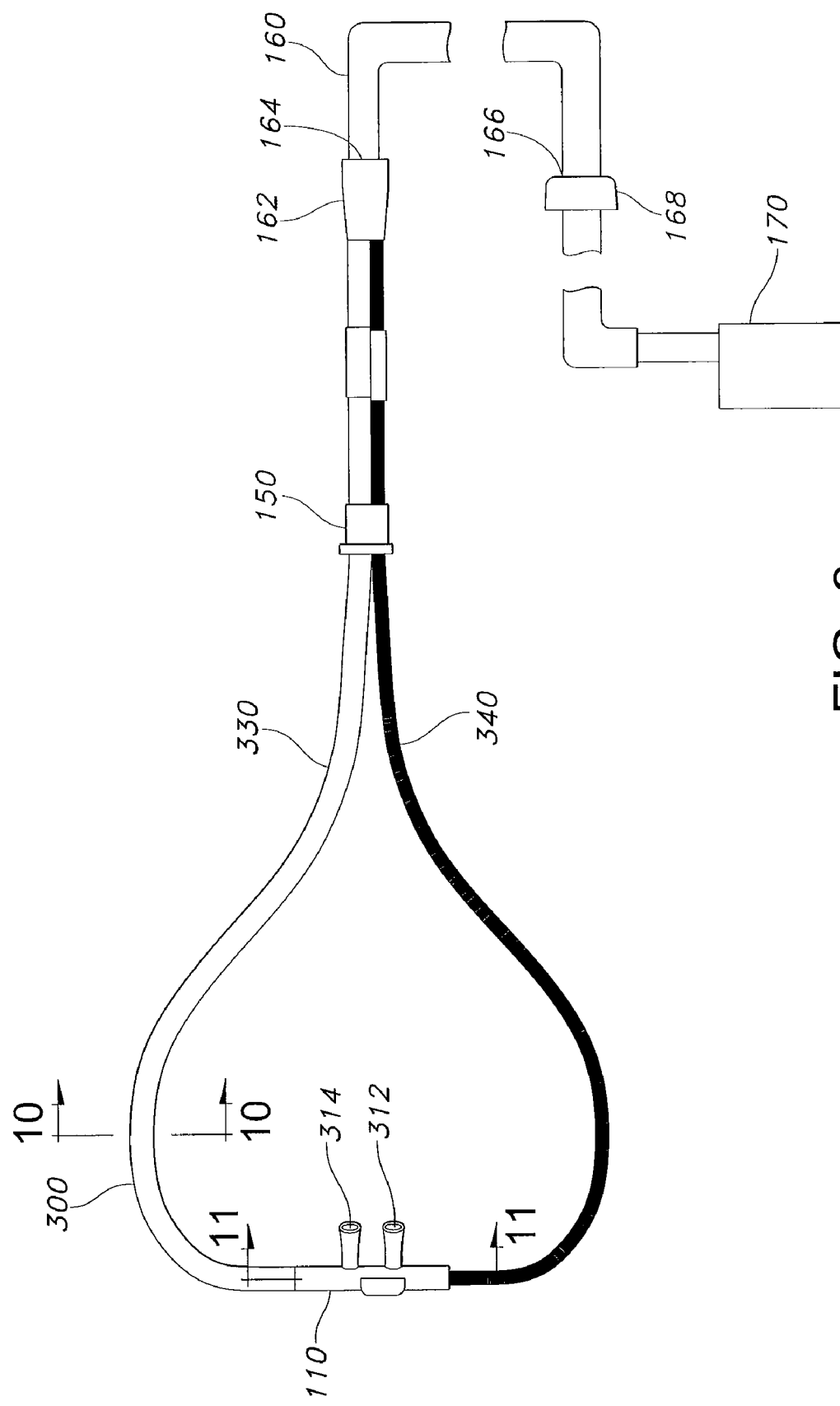
FIG. 9 is a schematic view of a third embodiment of a nasal cannula according to the present invention.
Figure 10:
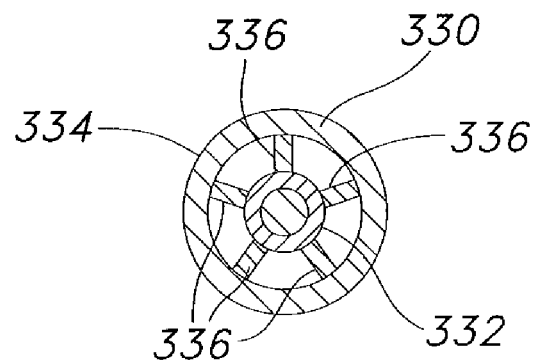
FIG. 10 is a sectional view of a lumen of the nasal cannula taken along lines 10-10 of FIG. 9.
Figure 11:
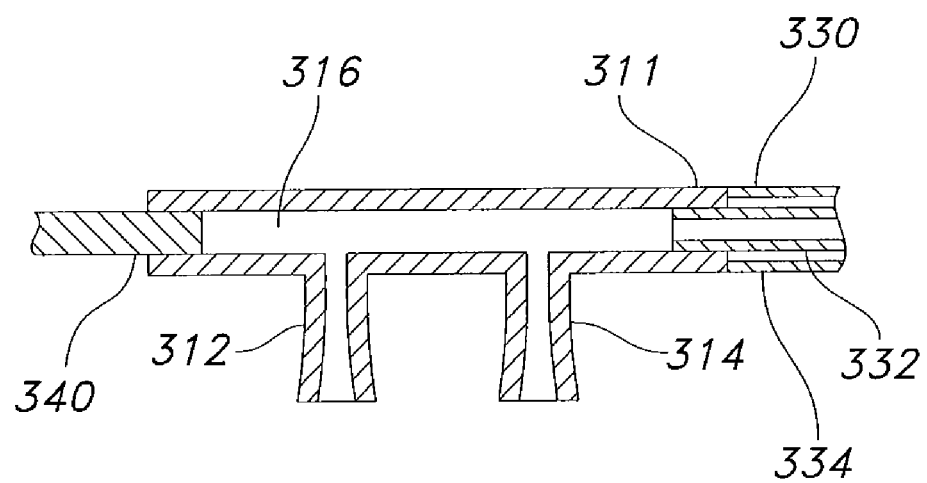
FIG. 11 is a sectional view of the nasal cannula taken along lines 11-11 of FIG. 9.

Still another embodiment of a nasal cannula 300 is shown generally in FIGS. 9-11. Nasal cannula 300 is similar to nasal cannula 200 described above, with the exception that, instead of first lumen 130, a first lumen 330 is used. First lumen 330 is a coaxial assembly that includes an inner lumen 332 and an outer lumen 334. Inner lumen 332 is used to provide breathing gas from source of breathing gas 170 to nasal prongs 312, 314. Outer lumen 334 does not transport any breathing gas or any other fluid, but acts instead as an insulator for the breathing gas in inner lumen 332. Air trapped within outer lumen 334 reduces heat loss from the breathing gas to atmosphere as the breathing gas is transmitted from source of breathing gas 170 to nasal prongs 312, 314.

Figure 18:
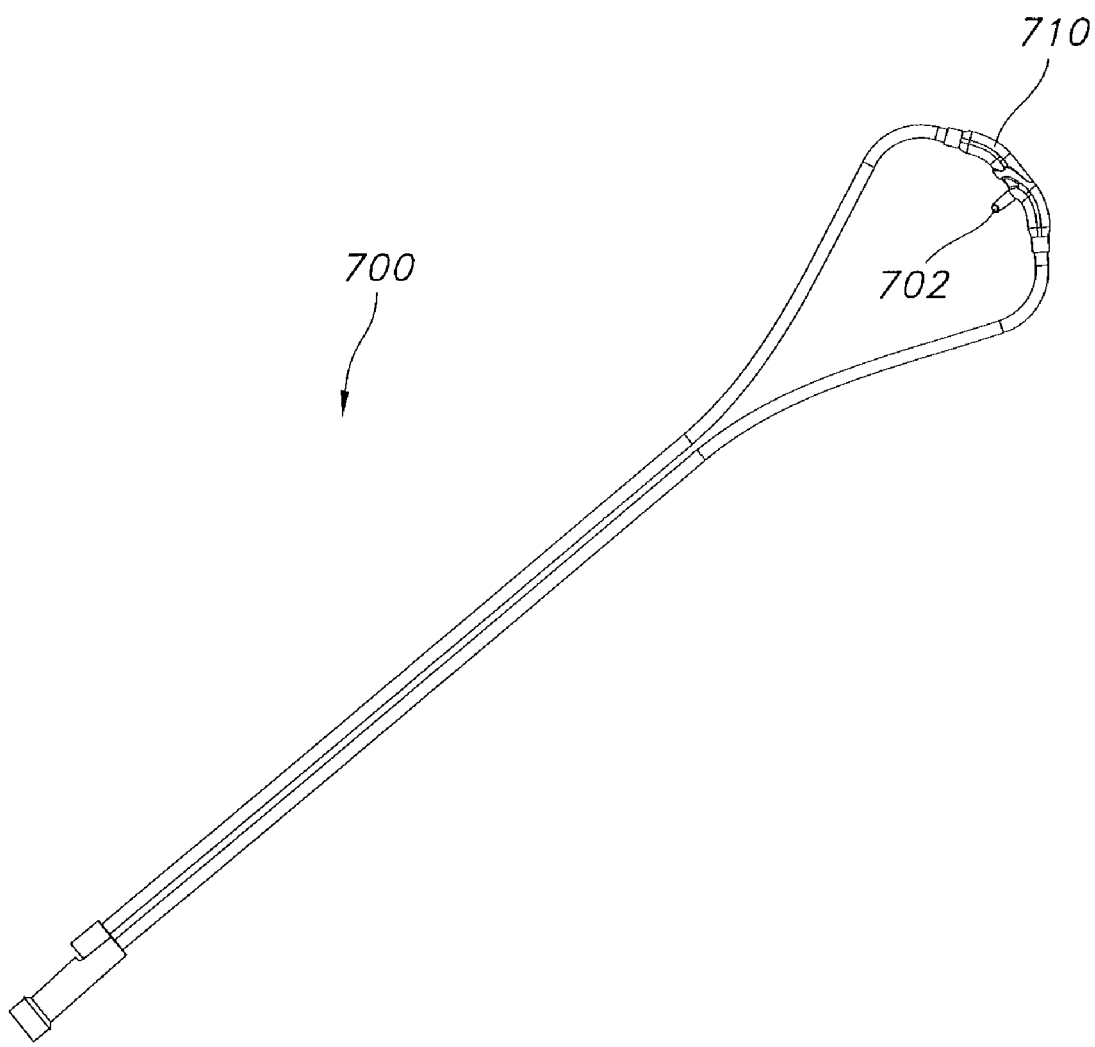
FIG. 18 is a perspective view of a nasal cannula according to another embodiment of the present invention.

Referring specifically to FIG. 10, a plurality of ribs 336 extend between inner lumen 332 and outer lumen 334 to maintain spacing between inner lumen 332 and outer lumen 334. While five ribs 336 are shown in FIG. 18, those skilled in the art will recognize that more or less than five ribs 336 may be used. Further, ribs 336 may extend the entire length of outer lumen 334, or ribs 336 may be spaced along the length of first lumen 330.

Inner lumen 332 may be co-extruded with outer lumen 334. Alternatively, inner lumen 332 may be separately extruded from outer lumen 334 and then inserted into outer lumen 334.

Inner lumen 332 is sized to fit within nasal element passageway 316 at first element end 311. Outer lumen 334 may butt up against first element end 311 as shown in FIG. 11, or, alternatively, outer lumen 334 may be inserted into nasal element passageway 316.

Second lumen 340 may preclude fluid flow therethrough, such as flexible member 150 discussed above. Alternatively, second lumen 340 may be constructed similarly to lumen 330 and reduces rainout due to the insulated nature of the lumen. Nasal cannula 300 may be worn and used in the same manner as nasal cannula 100 as described above.

Figure 12:
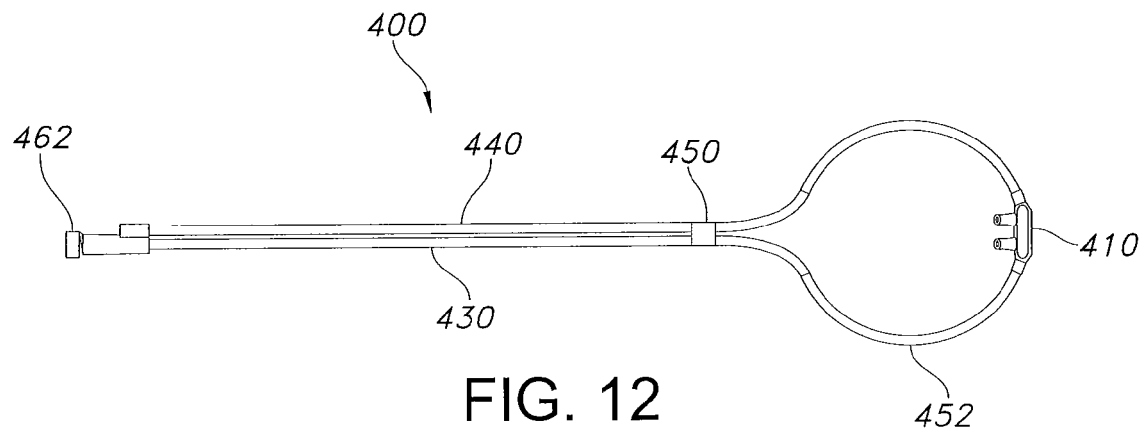
FIG. 12 is a top plan view of a nasal cannula according to a fourth embodiment of the present invention.
Figure 13:
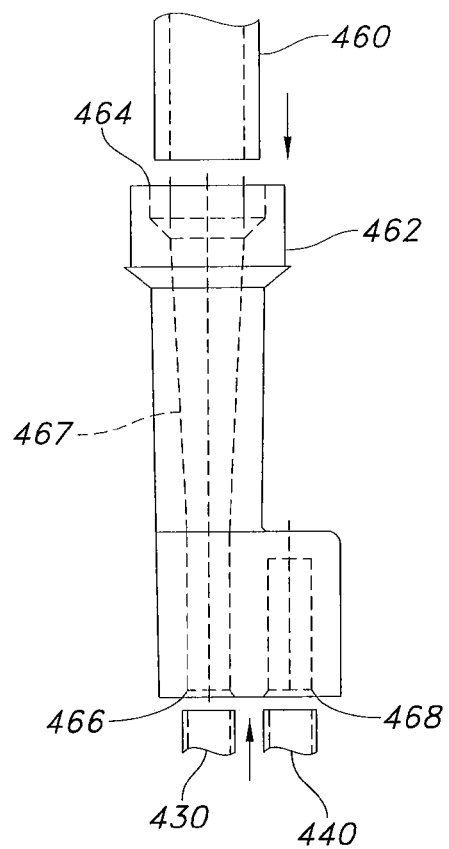
FIG. 13 is an enlarged top plan view of a connector used in the nasal cannula shown in FIG. 12.

Still another embodiment of a nasal cannula 400 is shown generally in FIGS. 12 and 13. Nasal cannula 400 is similar to nasal cannula 100 above. Instead of connector 140, however, a connector 462, shown in detail in FIG. 13, is used. Connector 462 includes an inlet 464, which is coupled to single tubing portion 460. Connector 462 also includes an outlet 466 and a through passage 467 that extends between inlet 464 and outlet 466, which provides fluid communication from single tubing portion 460 to a first lumen 430.

Connector 462 further includes a receiver 468, which is coupled to a second lumen 440. Receiver 468 does not provide fluid communication directly between single tubing portion 460 and second lumen 440, but instead closes off second lumen 440 to preclude fluid flow through second lumen 440.

Nasal cannula 400 also includes a collar 450 that encompasses first and second lumens 430, 440 therein, forming a loop 452 in nasal cannula 400, as shown to the right of collar 450 in FIG. 12. Collar 450 is adjustable along the lengths of first and second lumens 430, 440 to allow the patient to tighten or loosen nasal cannula 400 against his/her body.

Initially, breathing gas is supplied from a breathing gas source (not shown) to single tubing portion 460. The breathing gas flows from single tubing portion 460, through connector 462, to first lumen 430. The breathing gas flows through first lumen to nasal element 410. Some of the breathing gas is inhaled by the patient. A remaining portion of the breathing gas flows from nasal element 410 to second lumen 440. Since second lumen 440 is dead-headed at receiver 468 in connector 462, flow of the breathing gas through second lumen 440 stops, and the breathing gas must all discharge from nasal cannula 400 through nasal element 410 for inhalation by the patient.

Nasal cannula 400 may be worn and used in the same manner as nasal cannula 100 as described above. An advantage of retaining second lumen 440 is that the presence of second lumen 440 provides a means for the patient to retain nasal cannula 400 in place during use, similar to the way cannula 100 is shown being worn by patient 10 in FIG. 1.

Figure 14:
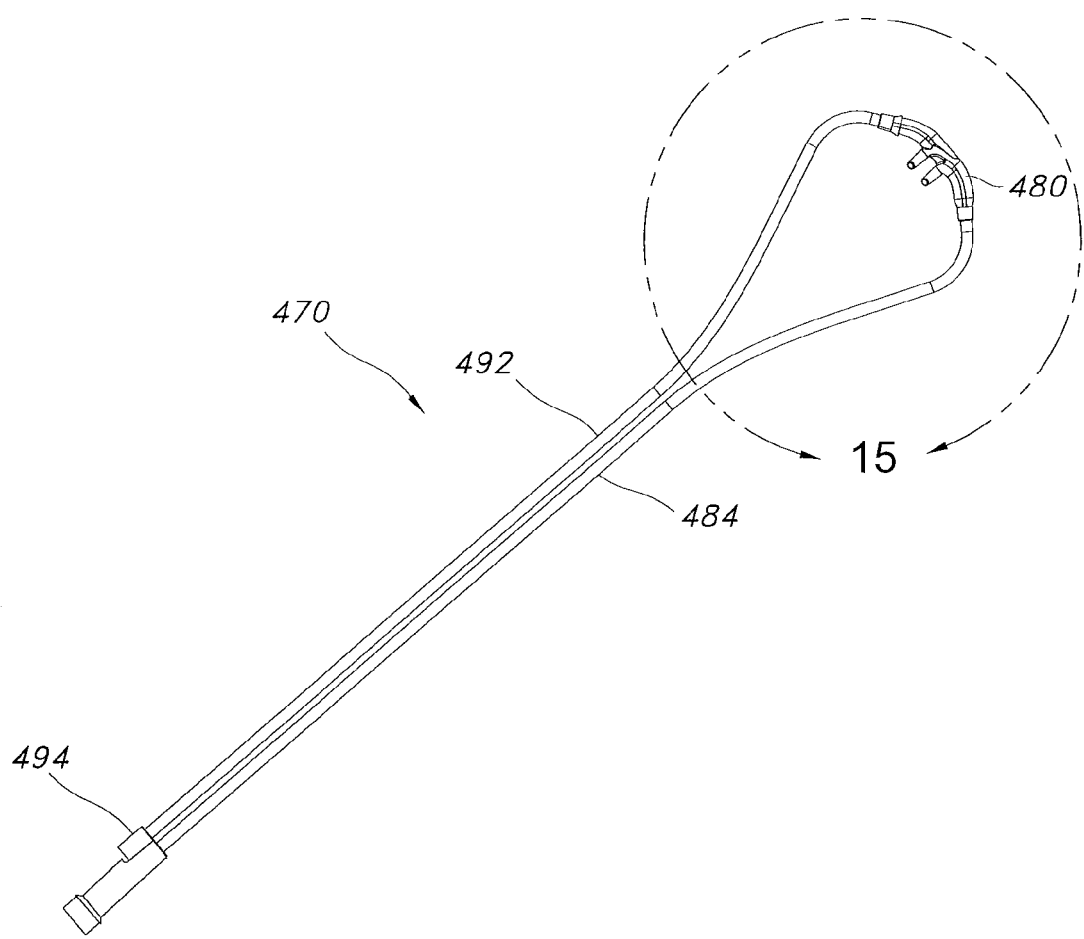
FIG. 14 is a perspective view of a nasal cannula according to another embodiment of the present invention.
Figure 15:
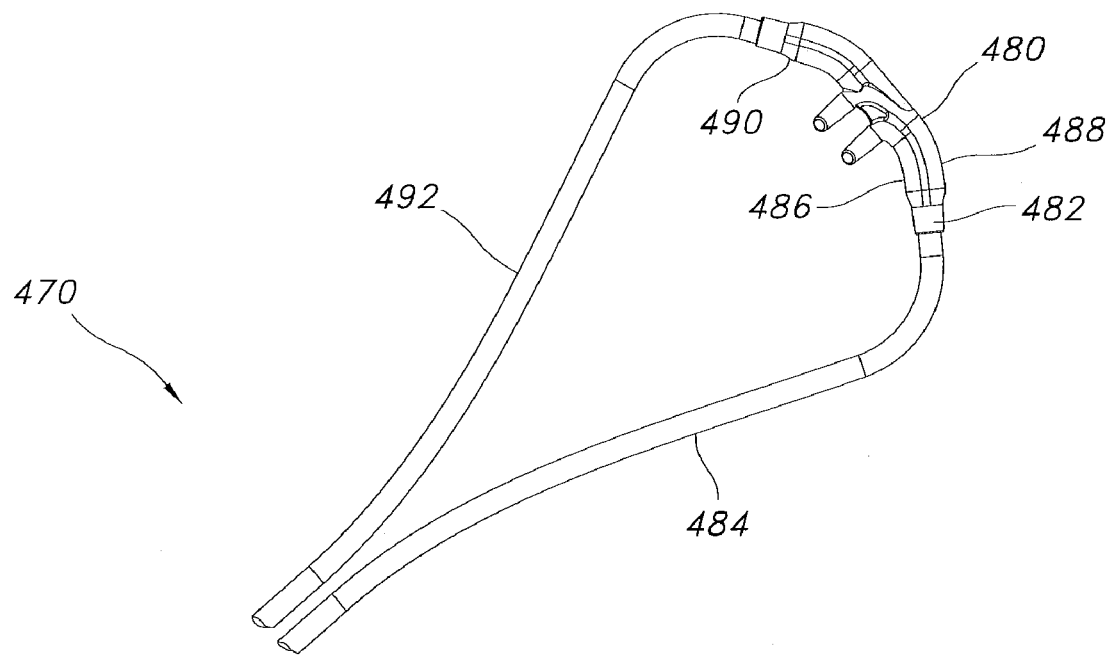
FIG. 15 is an enlarged portion of the cannula of FIG. 14, taken along line 15 of FIG. 14.

A nasal cannula 470 according to another embodiment of the present invention is shown in FIGS. 14 and 15. Nasal cannula 470 is similar to nasal cannula 400 described above and shown in FIGS. 12 and 13, but instead of using nasal element 410, nasal cannula 470 uses nasal element 480.

Nasal element 480 includes a cylindrical supply end 482 that is coupled to a breathing gas supply lumen 484. A pair of nasal lumens 486, 488 extends distally from supply end 482 and are in fluid communication with lumen 482. Nasal lumens 486, 488 each smoothly curve about ninety degrees and provide a smooth transition of breathing gas flow within nasal lumens 486, 488. The inner lumen of each of nasal lumens 486, 488 tapers from a larger diameter to a smaller diameter from supply end 482 to a respective discharge end to the user, with a generally constant wall thickness.

Nasal element 480 also includes an outlet 490 that is in fluid communication with a second lumen 492. Breathing gas that is not inhaled by a user through nasal lumens 486, 488 flows into second lumen 492 to a receiver 494, which is coupled to second lumen 4920. Receiver 494 does not provide fluid communication directly between a breathing gas supply (not shown) and second lumen 492, but instead closes off second lumen 492 to preclude fluid flow through second lumen 492.

Figure 16:
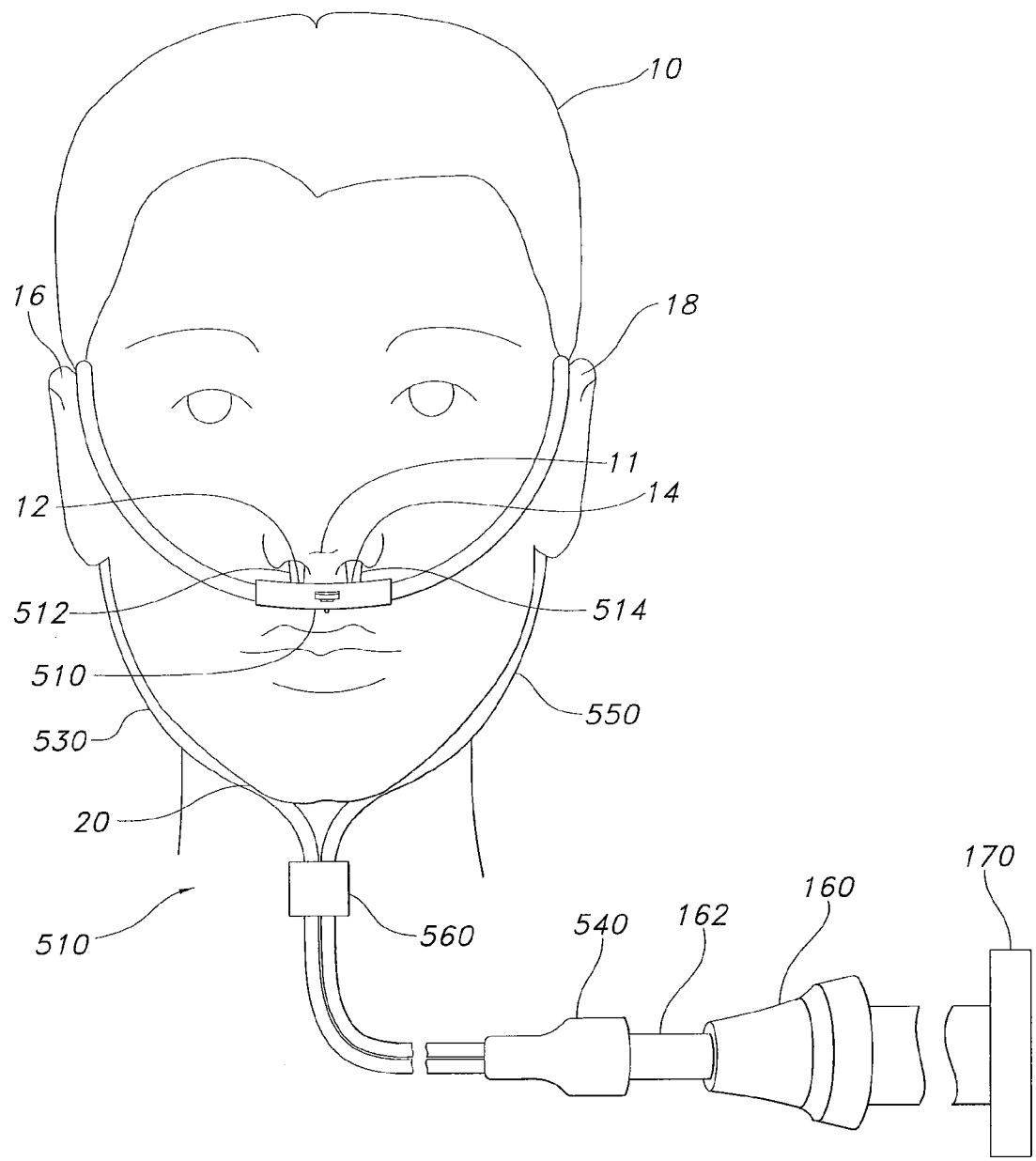
FIG. 16 is a front elevation view of an alternative embodiment of a nasal cannula according to the present invention in use on a patient.

Yet another embodiment of the present invention is shown in FIG. 16. A nasal cannula 500 includes a first lumen 530 and a second lumen 550 that are each coupled at a distal end to a nasal insertion member 510 having nasal prongs 512, 514. Each of nasal prongs 512, 514 is inserted into a respective nare 12, 14 of patient 10. A proximal end of each of first lumen 530 and second lumen 550 is coupled to a connector 540. Connector 540 is releasably coupled to a delivery tube 162. Delivery tube 162 is desirably approximately two (2) meters long or less to reduce temperature gradient in the breathing gas as the breathing gas flows through delivery tube 162. A reduction in the temperature gradient reduces rainout within delivery tube 162. Delivery tube 162 is coupled to humidification cartridge 170 via adapter 160.

Nasal cannula 500 also includes a collar 560 that encompasses first and second lumens 530, 550 therein, forming a loop in nasal cannula 500, as shown in FIG. 12. Collar 560 is adjustable along the lengths of first and second lumens 530, 550 to allow the patient to tighten or loosen nasal cannula 500 against his/her body. As shown in FIG. 12, collar 560 is slidable along first and second lumens 530, 550 toward patient 10 so that lumens 530, 550 are disposed against the patient's skin.

In use, nasal cannula 500 is attached to patient 10 as shown in FIG. 12, with first lumen 530 disposed over right ear 16 and second cannula 550 disposed over left ear 18. Nasal insertion member 510 is place under patient's nose 11 such that each of nasal prongs 512, 514 is inserted into a respective nare 12, 14 of patient 10. Collar 560 is slid distally along first lumen 530 and second lumen 550 so that first lumen 530 and second lumen 550 distal of collar 560 are disposed against the patient's skin, and more specifically, under and against patient's lower jaw 20, thereby reducing the temperature gradient of the heated and humidified breathing gas along the portions of first lumen 530 and second lumen 550 that are in contact with the patient's skin. Conductive heat transfer from the patient's skin to first lumen 530 and second lumen 550 reduces rainout within first lumen 530 and second lumen 550.

Heated and humidified breathing gas is provided from humidification cartridge 170. The heated and humidified gas flows through delivery tube 162 to nasal cannula 500, where the gas is delivered to patient 10 for inhalation.

Nasal cannula 500 may be sized to the particular patient 10 to minimize the length of cannula 500 between collar 560 and connector 540. The minimization of the length of cannula 500 helps to reduce the temperature gradient of breathing gas flowing through cannula 500, further reducing rainout.

While nasal cannulae 100, 200, 300, 400, 500 are all shown with two nasal prongs, those skilled in the art will recognize that nasal cannulae with a single nasal prong, such as the cannulae disclosed in U.S. patent application Ser. No. 11/943, 793, filed on even date, which is incorporated herein by reference, may be used without departing from the scope and spirit of the present invention. Alternatively, single prong nasal cannulae 600, 700 disclosed in FIGS. 17 and 18 below may be used.

Figure 17:
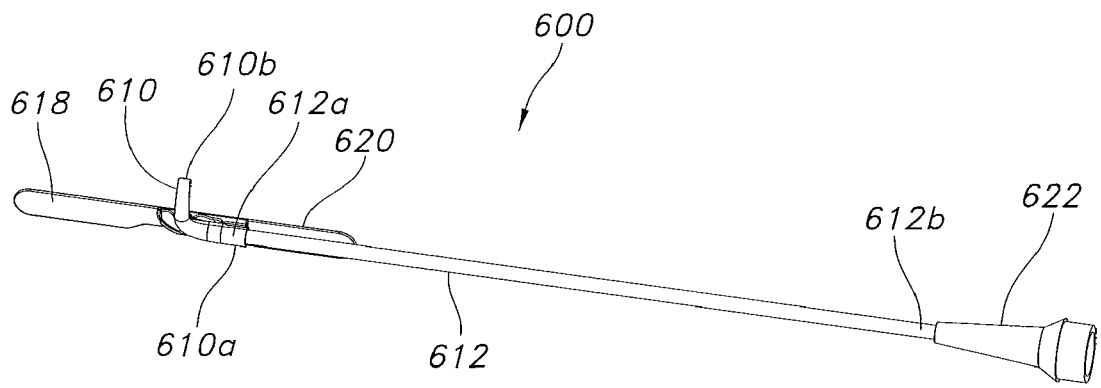
FIG. 17 is a perspective view of a nasal cannula according to another embodiment of the present invention.
Figure 17A:
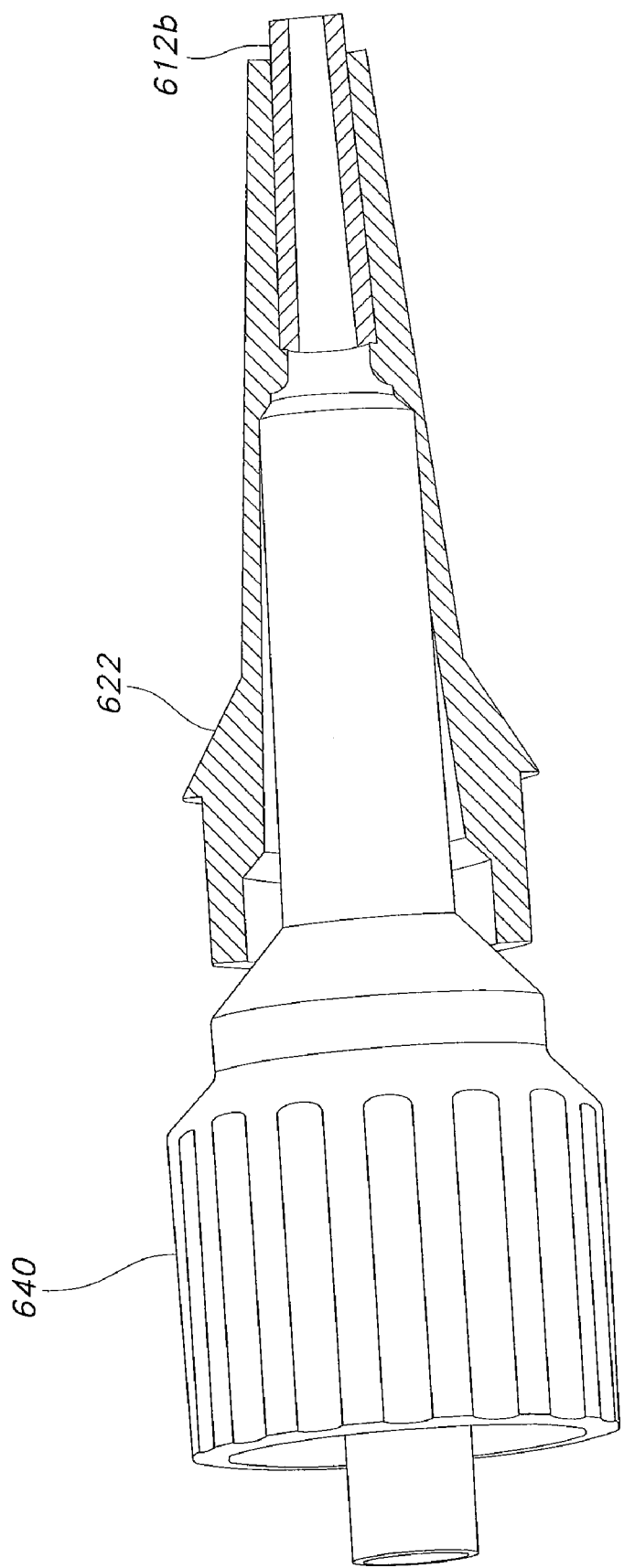
FIG. 17A is a perspective view, partially in section of a coupling between the nasal cannula of FIG. 17 and a delivery tube according to the present invention.

FIG. 17 shows yet another embodiment of a cannula 600 according to the present invention. Cannula 600 includes a single prong nasal element 610 extending from a first end 612a of a single lumen 612. Nasal element 610 has a coupled end 610a that is fixedly coupled to lumen 612. Nasal element 610 also includes a free end 610b that is inserted into a user's nare (not shown). Free end 610b extends at an angle, such as about ninety degrees, from coupled end 610a. Nasal element 610 changes direction via a smooth curve between coupled end 610a and free end 610b. An inner lumen of single nasal element 610 tapers from a larger diameter to a smaller diameter from coupled end 610a to free end 610b, with a generally constant wall thickness. A second end 612b of lumen 612 includes a hub 622 that is releasably connectable to a delivery tube fitting 640. A connection between hub 622 and fitting 640 for the delivery tube is shown in FIG. 17A. The inner diameter of lumen 612 is smaller than the inner diameter of delivery tube fitting 640.

Adhesive strips 618, 620 extend from nasal element 610. A first adhesive strip 618 extends away from lumen 612 and a second adhesive strip 620 extends along lumen 612. Adhesive strips 618, 620 are used to releasably secure cannula 600 to a user during use. Cannula 600 may be applicable for pediatric and/or neo-natal use, where it may be impractical to attempt to configure lumen 612 over the user's ear.

An alternative embodiment of a nasal cannula 700 according to an embodiment of the present invention is shown in FIG. 18. Cannula 700 is similar to nasal cannula 470 described above and shown in FIGS. 14 and 15, with the exception that, instead of two nasal lumens 486, 488 used in nasal cannula 470, nasal cannula 700 includes a nasal element 710 with only a single nasal prong 702. The structures of nasal prongs 290, 480, 610, and 702, with their smooth curves, provide for a smooth flow of breathing gas to the user, which minimizes noise of the breathing gas as it flows though the respective nasal prongs 290, 480, 610, and 702. The resulting noise reduction is especially critical for high flow rates during which noise becomes more pronounced than would be present, or audible, at lower flow rates. Also, the taper of the inner lumens in nasal prongs 290, 480, 610, and 702 also eliminates any breathing gas expansion area that may induce rainout. The various embodiments of nasal cannulae 100, 200, 280, 300, 400, 470, 600, and 700 are believed to reduce residence time of breathing gas flowing through the respective cannulae, which results in less time for the breathing gas to cool as it flows through the cannulae. The reduction of time for the breathing gas to cool reduces the likelihood of rainout within the respective cannulae. The embodiment of nasal cannula 500 uses the body heat of the user to reduce the temperature gradient between the inlet of cannula 500 and nasal prongs 512, 514, resulting in a reduced likelihood of rainout.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A system for delivering a heated and humidified gas to a patient comprising:
   a) a supply tube having a first supply tube end and a second supply tube end, the supply tube having a first inner diameter;
   b) a source of heated and humidified gas coupled to the first supply tube end for delivering gas through the first inner diameter of the supply tube;
   c) a connector in fluid flow communication with the second supply tube end; and
   d) a nasal cannula in fluid flow communication with the connector, the nasal cannula having:
      i) a nasal insertion member;
      ii) a lumen extending from one end of the nasal insertion member to the connector, the lumen providing fluid flow communication between the connector and the nasal insertion member; and
      iii) a flexible member extending to the connector from another end of the nasal insertion member opposite the one end of the nasal insertion member, the flexible member fixedly and directly coupled to the connector, the flexible member comprising a solid, non-lumen member that completely blocks fluid flow communication between the connector and the nasal insertion member.

2. The system according to claim 1, wherein the flexible member is adapted to be disposed over an ear of the patient.

3. The system according to claim 1, wherein the supply tube comprises an inner lumen and an outer lumen.

4. The system according to claim 3, wherein the outer lumen of the supply tube contains an insulating fluid.

5. A nasal cannula comprising:
   a nasal element having a first element end, a second element end, and a generally tubular body extending between the first element end and the second element end;
   a lumen having a first lumen end in fluid flow communication with the first element end, and a second lumen end;
   a connector having a first connector end in fluid flow communication with the second lumen end; and
   a flexible medium having a first solid closed end fixedly and directly coupled to the second element end and a second solid closed end fixedly and directly coupled to the first connector end.

6. The nasal cannula according to claim 5, wherein the flexible medium comprises a second lumen extending between the first closed end and the second closed end.

7. The nasal cannula according to claim 5, wherein the connector comprises a first inner diameter and the second lumen end comprises a second inner diameter, smaller than the first inner diameter.

8. The nasal cannula according to claim 5, wherein the lumen comprises an inner lumen and an outer lumen.

9. The nasal cannula according to claim 8, wherein the outer lumen contains an insulating fluid.

* * * * *